United States Patent
Han et al.

(10) Patent No.: US 9,035,092 B2
(45) Date of Patent: May 19, 2015

(54) PROCESS FOR THE (AMM)OXIDATION OF LOWER MOLECULAR WEIGHT ALKANES AND ALKENES

(75) Inventors: Scott Han, Lawrenceville, NJ (US); Edward C. Bayer, Philadelphia, PA (US); Andrew M. Lemonds, Schwenksville, PA (US); Daniel J. Martenak, Perkasie, PA (US); Nelson I. Quiros, Houston, TX (US)

(73) Assignee: Rohm and Haas Company

( * ) Notice: Subject to any disclaimer, the term of this patent is extended or adjusted under 35 U.S.C. 154(b) by 0 days.

(21) Appl. No.: 14/345,491

(22) PCT Filed: Aug. 23, 2012

(86) PCT No.: PCT/US2012/052042
§ 371 (c)(1),
(2), (4) Date: Mar. 18, 2014

(87) PCT Pub. No.: WO2013/048646
PCT Pub. Date: Apr. 4, 2013

(65) Prior Publication Data
US 2014/0350298 A1 Nov. 27, 2014

Related U.S. Application Data

(60) Provisional application No. 61/540,571, filed on Sep. 29, 2011.

(51) Int. Cl.
*C07C 51/25* (2006.01)
*C07C 253/24* (2006.01)
*C07C 253/26* (2006.01)
*C07C 51/215* (2006.01)

(52) U.S. Cl.
CPC ............. *C07C 51/252* (2013.01); *C07C 253/24* (2013.01); *C07C 253/26* (2013.01); *C07C 51/215* (2013.01)

(58) Field of Classification Search
CPC .... C07C 51/252; C07C 51/16; C07C 51/215; C07C 57/04; C07C 253/24; C07C 253/26
USPC ......................................................... 562/546
See application file for complete search history.

(56) References Cited

U.S. PATENT DOCUMENTS

| | | |
|---|---|---|
| 6,383,978 B1 | 5/2002 | Bogan, Jr. |
| 6,403,525 B1 | 6/2002 | Chaturvedi et al. |
| 6,407,031 B1 | 6/2002 | Chaturvedi et al. |
| 6,407,280 B1 | 6/2002 | Chaturvedi et al. |
| 6,461,996 B2 | 10/2002 | Chaturvedi et al. |
| 6,472,552 B1 | 10/2002 | Bogan, Jr. |
| 6,504,053 B1 | 1/2003 | Chaturvedi et al. |
| 6,589,907 B2 | 7/2003 | Chaturvedi et al. |
| 6,624,111 B2 | 9/2003 | Chaturvedi et al. |
| 7,304,014 B2 | 12/2007 | Cavalcanti et al. |
| 7,345,198 B2 * | 3/2008 | Dubois et al. ................. 562/549 |
| 7,553,986 B2 * | 6/2009 | Bogan et al. ................. 558/319 |

OTHER PUBLICATIONS

Sie, S.T., "Consequences of catalyst deactivation for process design and operation", Applied Catalysis A: General, vol. 212, (2001) p. 129-151.

\* cited by examiner

*Primary Examiner* — Yong Chu (57) ABSTRACT

A process for producing unsaturated carboxylic acids or unsaturated nitriles by vapor phase oxidation reaction of their corresponding $C_3$ to $C_5$ alkanes, $C_3$ to $C_5$ alkenes, and mixtures thereof, as a hydrocarbon starting material, wherein the process performance is monitored and the path of gasses through catalyst beds is altered. Improved catalyst lifetimes may be achieved.

13 Claims, 1 Drawing Sheet

3 Stage STOIC Reactor Configuration

PROCESS FOR THE (AMM)OXIDATION OF LOWER MOLECULAR WEIGHT ALKANES AND ALKENES

CROSS-REFERENCE TO RELATED APPLICATIONS

This application claims priority from provisional application Ser. No. 61/540,571, filed Sep. 29, 2011, which is incorporated herein by reference in its entirety.

BACKGROUND OF THE INVENTION

The invention relates to a process for the selective oxidation of $C_3$ to $C_5$ alkanes and alkenes to their corresponding unsaturated carboxylic acids and unsaturated nitriles.

In virtually all catalytic processes, the stability, or useful lifetime, of a catalyst is critical to its economic viability in the process. In addition to activity and selectivity, catalysts that show extended lifetime benefits are highly preferred. In a cyclic fluid bed operation, a key economic factor is catalyst make-up rate, otherwise known as the rate of addition of fresh catalyst needed to maintain certain activity levels in the reactor. This make up rate is a key factor in the choice of catalyst for the process. In a fixed bed operation, typically long catalyst cycle times are desired for highest viability. Short cycle times require faster catalyst change-out resulting in economic penalties such as additional catalyst cost, down time to repack catalyst, and lost productivity.

In the oxidation of propylene or propane to acrylic acid, catalyst lifetime is a major factor in catalyst choice and process economics. Typically, catalyst lifetimes in the fixed bed commercial propylene-to-acrylic acid process are desired to reach at least 2 years in length, including any necessary catalyst regeneration steps. Extended catalyst lifetime is also desired for propane oxidation to acrylic acid as a similar fixed bed catalyst and process are used.

U.S. Pat. No. 7,553,986 discloses the staged oxygen intercondenser, hereinafter referred to as STOIC, process for oxidation of certain hydrocarbons, e.g. propane, to unsaturated carboxylic acids or unsaturated nitriles. Two- or three-stage processes may be used and show an advantage over single pass operation. Advantages stated are based on yield of acrylic acid.

It would be desirable to have a STOIC process operated under conditions capable of improving the useful life of the catalyst.

SUMMARY OF THE INVENTION

The process disclosed herein is such a process for producing unsaturated carboxylic acids or unsaturated nitriles by vapor phase oxidation reaction of their corresponding $C_3$ to $C_5$ alkanes, $C_3$ to $C_5$ alkenes, and mixtures thereof, as a hydrocarbon starting material, using a reaction system having at least two reaction zones arranged in series with one another and at least one catalyst capable of catalyzing the vapor phase oxidation reaction disposed in each of the at least two reaction zones, wherein at least one intermediate effluent stream exits a preceding one of the at least two reaction zones and is at least partially fed to a subsequent one of the at least two reaction zones, said process comprising the steps of:

feeding an initial feed stream comprising the hydrocarbon starting material into a feed point of a first reaction zone of the two reaction zones, separating the at least one intermediate effluent stream from the first reaction zone into at least an intermediate product stream comprising an oxidation product selected from the group consisting of an unsaturated carboxylic acid and an unsaturated nitrile, and an intermediate feed stream comprising at least one hydrocarbon starting material selected from the group consisting of an unreacted $C_3$ to $C_5$ alkane, an unreacted $C_3$ to $C_5$ alkene, and mixtures thereof;

feeding an oxygen-containing gas and the intermediate feed stream to a subsequent reaction zone;

the process further comprising:
a. determining the activity of the catalyst in at least one reaction zone;
b. monitoring the activity of the catalyst in each zone to determine the time when the catalyst in any zone has lost at least 25% of its activity;
c. after step b., altering the flow path of at least one of the feed streams such that at least one of the hydrocarbon starting material or the intermediate feed stream is fed to a new feed point, the new feed point being either a feed point of a different reaction zone or a different feed point of the same reaction zone, wherein the catalyst at that new feed point has a higher activity than the activity of the catalyst at the feed point to which the relevant feed was fed prior to this step c.

Surprisingly, the process increases catalyst lifetime relative to conventional staged operation.

DETAILED DESCRIPTION OF THE INVENTION

The process of the invention is an improvement on the STOIC process, and involves monitoring certain process conditions and, based on those conditions, changing the flow of materials through the process. The process of the invention employs an oxygen source, a hydrocarbon starting material and a catalyst. The process optionally employs steam and/or diluting gases. Ammonia is employed if a nitrile product is desired. The process of the invention is suitable for performing selective vapor phase catalytic oxidation of $C_3$ to $C_5$ alkanes and alkenes, and mixtures thereof, to their corresponding unsaturated carboxylic acids and unsaturated nitriles, including acrylic acid, methacrylic acid, acrylonitrile and methacrylonitrile. In this regard, the term "vapor phase catalytic oxidation" is intended to encompass simple oxidation, as well as ammoxidation and oxidative dehydrogenation.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.).

Also herein, the recitations of numerical ranges and/or numerical values, including such recitations in the claims, can be read to include the term "about." In such instances the term "about" refers to numerical ranges and/or numerical values that are substantially the same as those recited herein.

For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

The efficacy of chemical reaction processes, including the process of the present invention, may be characterized in terms of the "feed conversion" and the "product yield." More particularly, feed conversion, or simply "conversion," is the percentage of the total moles of feed (e.g., $C_3$ to $C_5$ alkanes and alkenes, such as propane and propylene, or a mixture thereof) that have been consumed by the reaction, regardless of what particular products were produced. The product yield, or simply "yield," is the percentage of the theoretical total moles of the desired product (e.g., unsaturated carboxylic acids or unsaturated nitrile, such as acrylic acid or acrylonitrile, respectively) that would have been formed if all of the feed had been converted to that product (as opposed to unwanted side products, e.g., acetic acid and $CO_x$ compounds). The aforesaid terms are generally defined as follows:

$$\text{feed conversion (\%)} = \frac{\text{moles of feed converted}}{\text{moles of feed supplied}} \times 100$$

$$\text{product yield (\%)} = \frac{\text{moles of product produced}}{\text{moles of feed supplied}} \times 100$$

The process employs multiple reaction zones. The overall yield of oxidation product from such multiple reaction zone (i.e., "multi-stage") reaction systems is cumulative relative to each reaction zone. In other words, for example, where such a reaction system has three reaction zones and the first reaction zone provides an oxidation product yield of about 35%, the second reaction zone provides about 20% yield, and the third reaction zone provides about 10%, then the overall yield of oxidation product by the system could be expected to be about 65%.

As used herein, the term "$C_3$ to $C_5$ alkane" means a straight chain or branched chain alkane having from 3 to 5 carbons atoms per alkane molecule. Examples of $C_3$ to $C_5$ alkanes include, for example, propane, butane and pentane. The term "$C_3$ to $C_5$ alkene" means a straight chain or branched chain alkene having from 3 to 5 carbons atoms per alkene molecule. Examples of $C_3$ to $C_5$ alkenes include, for example, propylene, butylene and pentene. As used herein, the term "$C_3$ to $C_5$ alkanes and alkenes" includes both of the aforesaid alkanes and alkenes. Similarly, when used herein in conjunction with the terms "$C_3$ to $C_5$ alkane," or "$C_3$ to $C_5$ alkene," or "$C_3$ to $C_5$ alkanes and alkenes," the terminology "a mixture thereof," means a mixture that includes a straight chain or branched chain alkane having from 3 to 5 carbons atoms per alkane molecule and a straight chain or branched chain alkene having from 3 to 5 carbons atoms per alkene molecule, such as, without limitation, a mixture of propane and propylene, or a mixture of n-butane and n-butylene. Mixtures of these hydrocarbons are often obtained from commercial processes such as steam cracking and fluid catalytic cracking.

The purity of the hydrocarbon starting material, i.e., the $C_3$ to $C_5$ alkane, the $C_3$ to $C_5$ alkene, or the mixture thereof, is not particularly limited, and an alkane containing air, carbon dioxide, or a lower alkane, such as methane, ethane, as impurities may be used without any particular problem. There is no limitation on the source of the hydrocarbon starting material. For example, the hydrocarbon starting material can be a commercially available material or can be generated as a by-product of alkane oxidation. Moreover, the alkane, regardless of source, and the alkene, regardless of source, may be blended as desired. Commercial grades of alkanes, alkenes, or mixtures of such alkanes and alkenes, may be used as starting material for the process of the present invention, although higher purities are advantageous from the standpoint of minimizing competing side reactions. Mixed $C_3$ to $C_5$ alkane/alkene feeds are generally more easily obtained and may include price incentives (e.g., lower separation costs) relative to pure $C_3$ to $C_5$ alkane feeds. For example, a mixture of alkane and alkene containing a lower alkene such as ethylene, a lower alkane such as methane or ethane, and air or carbon dioxide, as impurities, may be used without any particular problem.

As an alternative to a $C_3$ to $C_5$ alkane or alkene, an alkanol, such as isobutanol, which will dehydrate under the reaction conditions to form its corresponding alkene, i.e., isobutylene, may also be used as a feed material to the present process or in conjunction with the previously mentioned feed streams. Suitable alkanols include, but are not limited to, normal and branched alcohols such as, for example, ethanol, n- or iso-propanol, and n- or branched butanols. Other alternative feed-stocks include functionalized alkanes, alkyl halides, amines etc.

Without intending to limit the present invention in any way, another application of the process of the present invention is to produce an unsaturated nitrile. Such a process comprises reacting a $C_3$ to $C_5$ alkane, or a mixture of $C_3$ to $C_5$ alkanes and alkenes, containing at least 0.5% by weight of the $C_3$ to $C_5$ alkane, with ammonia in the presence of a suitable catalyst, as described hereinabove, to produce an unsaturated nitrile by vapor phase oxidation, in a single step.

In the production of such an unsaturated nitrile, as the starting material alkane, it is preferred to employ a $C_3$ to $C_5$ alkane such as ethane, propane, butane, isobutane, or pentane. However, in view of the industrial application of nitrites to be produced, it is preferred to employ a lower alkane having 3 or 4 carbon atoms, particularly propane and isobutane.

Similarly, as the hydrocarbon starting material mixture of alkane and alkene, it is preferred to employ a mixture of a $C_3$ to $C_5$ alkane and a $C_3$ to $C_5$ alkene, such as propane and propylene, butane and butylene, isobutane and isobutylene, or pentane and pentene. However, in view of the industrial application of nitriles to be produced, it is more preferred to employ a mixture of a lower alkane having 3 or 4 carbon atoms and a lower alkene having 3 or 4 carbon atoms, particularly propane and propylene, or isobutane and isobutylene. For example, without limitation, in the mixture of alkane and alkene, the alkane or alkene independently may be present in an amount of at least 0.1% by weight up to 95% by weight, including at least 0.5% by weight to 10% by weight, or even 0.5% by weight to 5% by weight, based on the total weight of the alkane and alkene, with the proviso that the total amount of alkane and alkene must equal 100%.

The detailed mechanism of the oxidation reaction of the present invention is not clearly understood, but the oxidation reaction is carried out by oxygen atoms present in the mixed metal oxide catalyst or by molecular oxygen present in the feed gas. Addition of the oxygen-containing gas to the starting materials provides molecular oxygen to the reaction system. In one embodiment of the invention, the oxygen source is an oxygen-containing gas. The term "oxygen-containing gas," as used herein, refers to any gas comprising from 0.01% up to 100% oxygen, including, for example, air. While the oxygen-containing gas may be pure oxygen gas, it is usually more economical to use an oxygen-containing gas such as air, since 100% $O_2$ purity is not particularly required.

Suitable diluting gases include, but are not limited to, one or more of: carbon monoxide, carbon dioxide, nitrogen, argon, helium, or mixtures thereof. A suitable molar ratio of the starting materials for the initial feed stream, ($C_3$ to $C_5$ alkane, $C_3$ to $C_5$ alkene, or a mixture thereof):(oxygen):(diluting gas):($H_2O$), would be, for example, (1):(0.1 to 10):(0 to 20):(0.2 to 70), for example, including but not limited to, (1):(1 to 5.0):(0 to 10):(5 to 40).

Where it is desired to produce unsaturated carboxylic acids, it is beneficial to include steam among the starting materials. In such a case, for example, a gaseous input stream comprising a mixture of an oxygen-containing gas and a steam-containing $C_3$ to $C_5$ alkane, or a steam-containing $C_3$ to $C_5$ alkene, or a steam-containing mixture thereof, may be used.

Any suitable catalyst may be used and would be selected based upon the particular $C_3$ to $C_5$ alkane, $C_3$ to $C_5$ alkene, or mixture thereof employed and the desired oxidation products. The catalyst may comprise a mixed metal oxide. As is well known in the art, the catalysts may be used alone, or they may also be used together with a carrier, or support, such as, without limitation, silica, alumina, titania, aluminosilicate or diatomaceous earth. Further, depending upon the scale or system of the reaction, they may be molded into a proper shape and/or particle size. The particular shape or geometry of the catalysts are not particularly limited in connection with the present invention. The selection of the catalysts, their shape, size and packing method, are well within the ability of persons having ordinary skill in the art. For example, suitable catalysts for a variety of vapor phase oxidation reactions are described fully in U.S. Pat. Nos. 6,383,978, 6,403,525, 6,407,031, 6,407,280, 6,461,996, 6,472,552, 6,504,053, 6,589,907 and 6,624,111. In one embodiment of the invention, the catalyst has essentially the same composition, before use, in at least 2 reaction zones.

Figure 1:
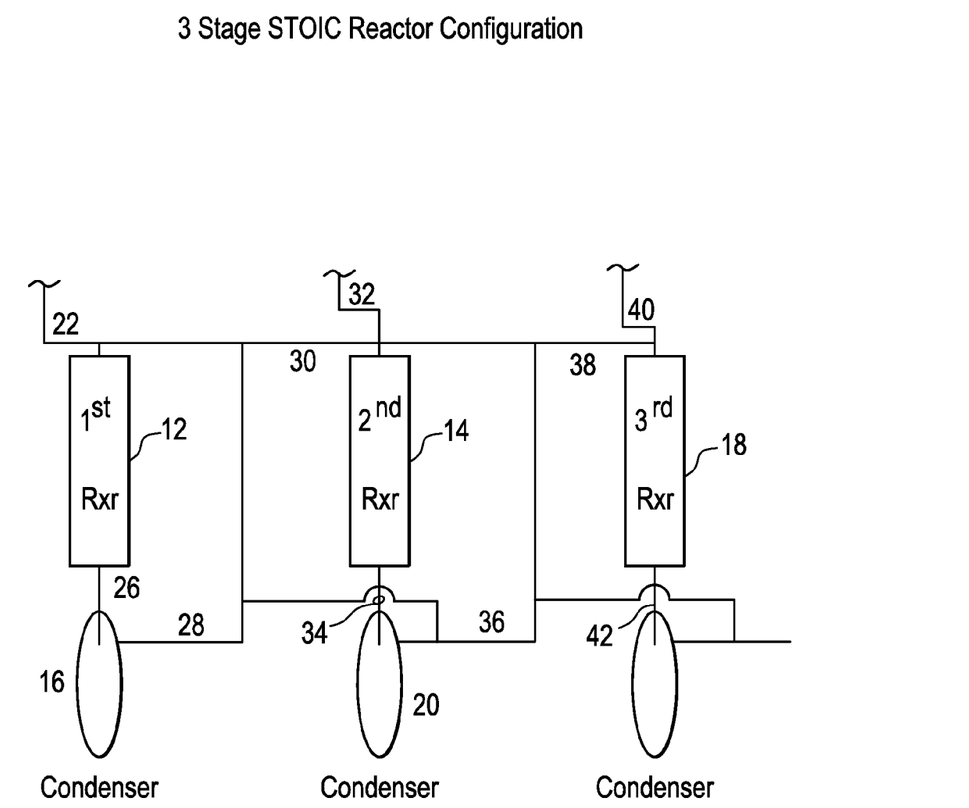
FIG. 1 is a schematic flow diagram of one embodiment of the process of the present invention.

With reference now to FIG. 1, a schematic representation is shown of a multi-stage catalytic vapor phase oxidation process, in accordance with the present invention, that is capable of converting a $C_3$ to $C_5$ alkane, a $C_3$ to $C_5$ alkene, or a mixture thereof (such as, for example, propane, or a mixture of propane and propylene), to an unsaturated carboxylic acid (such as acrylic acid) or an unsaturated nitrile (such as acrylonitrile) in a single reaction step. The process includes at least a first reaction zone (or "stage") 12 and a second reaction zone (or "stage") 14, which are arranged in series with one another such that the second reaction zone 14 is positioned downstream of the first reaction zone 12. The process of the present invention also includes a separator, such as a condenser 16, which is positioned intermediate to the first and second reaction zones 12, 14, for a purpose to be described in detail hereinafter.

As shown in FIG. 1, the process of the present invention may also include additional, optional reaction zones, such as a third reaction zone (or "stage") 18 arranged in series with and downstream of the second reaction zone 14. Where the process includes such additional reaction zones, it may also include additional separators, such as a third condenser 42 positioned after to the third reaction zone 18, for a purpose to be described in detail hereinafter. As used herein, an arrangement of reaction zones "in series" with one another means that the reaction zones are arranged such that at least a portion of the output stream of the first reaction zone is employed as at least a portion of the input stream of the second reaction zone and each successive reaction zone is similarly interconnected with the preceding reaction zone. It is noted that the portion of output stream that forms a portion of the input stream of each the successive reaction zone need not be the same with respect to amount, proportion, composition, temperature, etc., since these stream characteristics should be determined according to the requirements of the particular overall reaction system and each reaction zone, as would be readily determinable by those having ordinary skill in the art. In particular, it is noted that the reaction zones 12, 14, 18 of the present invention are arranged in series with one another, with the separators 16, 20 positioned intermediate to successive reaction zones, 12, 14 and 18, respectively, for purposes that will become clear hereinafter.

Any type of reactors that are suitable for performing the desired vapor phase oxidation reactions may be used to contain, or hold, the reaction zones 12, 14, 18 in accordance with the process of the present invention. Shell-and-tube reactors, for example and without limitation, are suitable for use in connection with the process of the present invention.

A three reactor configuration is shown in FIG. 1 as an example. The number of reaction stages used, however, need not be limited to three and may be greater if necessary and practical. The most advantageous arrangement of equipment can be selected for the desired application according to methods well known to those skilled in the art.

In addition, at least one catalyst bed (not shown, per se) is contained within each of reaction zones 12, 14 and 18, and comprises at least one catalyst (not shown) capable facilitating the desired vapor phase oxidation reaction. The catalyst beds may be of different types including but not limited to, moving-bed, and fixed-bed, which is preferred.

Separators suitable for use with the present invention include any suitable fluid separator capable of separating a gaseous product stream into multiple streams according to composition, such as separating a gaseous output stream into a first stream containing primarily the desired reaction product(s) and a second stream containing primarily unreacted materials and by-products. For example, while not intending to be limited, the separator 16, 20 may be a partial condenser, such as a conventional heat exchanger, capable of cooling the gaseous output stream sufficiently to condense and separate out at least a portion of the lowest boiling point components of the gaseous output stream. The coolant in such a condenser may be any heat transfer fluid, for example, without limitation, cooling tower water having a temperature between 85° F. and 105° F. (29° C. to 40° C.), or chilled water having a temperature between 32° F. and 40° F. (0° C. and 5° C.). In addition, for example, the separators may include gas absorbers and/or gas adsorbers. The exit gas from the reaction zone may be contacted with a solvent or process stream of suitable composition to quench the vapor and promote efficient separation.

Optionally the condensed phase from separators 16, 20, 42 can be stabilized with a polymerization inhibitor to protect the condensed phase against undesirable fouling due to polymer formation. Examples of suitable polymerization inhibitors include phenothiazines and its derivatives, 2,2,6,6-tetramethyl piperidin-1-oxyl stable free radical and its derivatives, phenols such as hydroquinone, substituted phenols, and other such compounds known to those skilled in the art of polymerization inhibition. Inhibitors can be used individually or in combination of two or more components.

Suitable starting materials, which are discussed herein and which are readily determinable by persons having ordinary skill in the art, are fed into the first reaction zone 12. In the first reaction zone 12, the starting materials come into contact with the catalyst and react to form the desired oxidation products, as well as various side products and by-products, according to the particular types of $C_3$ to $C_5$ alkanes and alkenes used.

Suitable starting materials for the process of the present invention depend upon the desired oxidation product and typically include, but are not limited to, a $C_3$ to $C_5$ alkane, a $C_3$ to $C_5$ alkene, or a mixture thereof, and an oxygen-containing gas, as well as, optionally, steam, diluting gases and ammonia. The starting materials may be added separately and simultaneously to the first reaction zone 12, or they may be mixed and fed to the first reaction zone 12 as one or more combined streams. For example, as explained in further detail hereinafter, the initial feed stream 22, shown in FIG. 1 may be a combined stream comprising an oxygen-containing gas such as, in this case air, and a $C_3$ to $C_5$ alkane, a $C_3$ to $C_5$ alkene, or a mixture thereof. The initial feed stream 22 may also include optional supplemental feed gases such as, for example, steam-containing gases and/or ammonia-containing gases, depending upon the particular oxidation products desired. The optional supplemental streams may comprise additional $C_3$ to $C_5$ alkane, $C_3$ to $C_5$ alkene, or a mixture thereof.

The feed gases, i.e. a $C_3$ to $C_5$ alkane, a $C_3$ to $C_5$ alkene, or a mixture thereof, and an oxygen-containing gas, as well as, optionally, steam, diluting gases and ammonia may be added separately and simultaneously to the first reaction zone 12, or they may be mixed and fed to the first reaction zone 12 in any combination. The steam to be employed may be introduced in any suitable manner.

When steam is supplied together with the mixture of $C_3$ to $C_5$ alkanes and alkenes, as starting material gas, the selectivity for an unsaturated carboxylic acid generally is distinctly improved, and the unsaturated carboxylic acid can be obtained in good yield. However, the conventional technique utilizes a diluting gas, as described above, for the purpose of diluting the starting material. Such a diluting gas is used to adjust the space velocity, the oxygen partial pressure and the steam partial pressure, as will be readily understood by persons having ordinary skill in the art.

Where it is desired to produce unsaturated nitriles, the starting materials must include ammonia. In such cases, it is possible to use an initial feed stream 22, which is a gas mixture comprising a $C_3$ to $C_5$ alkane, a $C_3$ to $C_5$ alkane, or a mixture thereof, ammonia (not shown), and an oxygen-containing gas. Alternatively, an oxygen-containing gas, a gaseous mixture comprising a $C_3$ to $C_5$ alkane, or a $C_3$ to $C_5$ alkene or a mixture thereof, and ammonia may be supplied as separate feed streams (not shown) to the first reaction zone 12.

In the process of the present invention, as the hydrocarbon starting material, it is suitable to use a mixture of $C_3$ to $C_5$ alkane and $C_3$ to $C_5$ alkene, for example, propane and propylene, isobutane and isobutylene, or n-butane and n-butylene. According to the present invention, from such a mixture of an alkene and an alkane, an unsaturated carboxylic acid such as an alpha, beta-unsaturated carboxylic acid can be obtained in good yield. For example, when propane and propylene, or isobutane and isobutylene, are used as the starting material mixture of alkane and alkene, acrylic acid or methacrylic acid will be obtained, respectively, in good yield. In the mixture of alkane and alkene, the alkane is present in an amount of at least 0.5% by weight up to 95% by weight, preferably at least 0.5% by weight to 10% by weight; most preferably, 0.5% by weight to 5% by weight.

It is also possible to operate the process of the present invention substantially in the absence of molecular oxygen. In such a case, it is preferred to adopt a method wherein a part of the catalyst is appropriately withdrawn from the reaction zone from time to time, then sent to an oxidation regenerator, regenerated and then returned to the reaction zone(s) for reuse. As the regeneration method of the catalyst, a method may, for example, be employed that comprises contacting an oxidative gas such as oxygen, air or nitrogen monoxide with the catalyst in the regenerator usually at a temperature of from 300° to 600° C.

With reference again to FIG. 1, a first effluent stream 26 exits the first reaction zone 12 and typically contains, but is not limited to, one or more oxidation products (e.g., unsaturated carboxylic acids and unsaturated nitriles) and non-products including, for example, oxygen, one or more alkanes and/or alkenes, water and, possibly, ammonia, depending upon the starting materials used. The first effluent stream 26 may also contain reaction by-products such as, for example, but not limited to, acetic acid and carbon dioxide.

In accordance with the present invention, at least a portion of the one or more oxidation products is separated from the first effluent stream 26, for example, by using a separator, such as the condenser 16 shown in FIG. 1, to produce an intermediate product stream 28 and an intermediate feed stream 30 (see FIG. 1). The intermediate product stream 28 typically contains, but is not limited to, at least a portion of the one or more oxidation products from the first effluent stream 26, as well as other condensables, such as organic acids, aldehydes, ketones, and water. The intermediate product stream 28 may be fed to additional processing apparatus (not shown) to undergo further separation and purification processes. The intermediate feed stream 30 contains, but is not limited to, at least a portion of the unreacted oxygen, unreacted $C_3$ to $C_5$ alkane or alkene, or mixture thereof, and possibly reaction by-products such as acetic acid and carbon dioxide, and, possibly, unreacted water and unreacted ammonia, depending upon the starting materials used.

As shown in FIG. 1, the intermediate feed stream 30 is fed into the second reaction zone 14, along with additional oxygen-containing gas 32. More particularly, the additional oxygen-containing gas 32 may be first combined with the intermediate feed stream 30 and then fed together, as a combined stream (see FIG. 1) to the second reaction zone 14. Alternatively, the additional oxygen-containing gas 32 may be fed to the second reaction zone 14 as a separate feed stream (not shown). Oxygen-containing gas 32 can optionally contain supplemental $C_3$ to $C_5$ alkane or alkene, or mixture thereof if so desired. In the second reaction zone 14, the unreacted $C_3$ to $C_5$ alkane or alkene, or mixture thereof, and the oxygen (including the unreacted oxygen already present in the intermediate feed stream 30, as well as the additional oxygen contributed by the oxygen-containing gas 32) come into contact with the at least one catalyst in the second reaction zone 14 and react with one another to form the desired oxidation products, as well as various side products and by-products, according to the particular types of alkanes and alkenes used.

A second effluent stream 34 (see FIG. 1) exits the second reaction zone 14 and typically contains, but is not limited to, one or more oxidation products (e.g., unsaturated carboxylic acid and unsaturated nitrile), and non-products and by-products as mentioned hereinabove. The second effluent stream 34 may be fed to additional processing apparatus (not shown) to undergo separation and purification processes as is well-known to persons having ordinary skill in the art, to recover the one or more oxidation products.

The cumulative yield (%) of a particular oxidation product produced by a multi-stage oxidation reaction process, such as the process of the present invention, is calculated by adding the numbers of moles of the particular oxidation product present in each of the effluent streams, dividing this sum by the number of moles of alkane (or alkane and alkene) fed to the process, and multiplying the result by 100. For example, the following formula is suitable for calculating the cumulative yield of oxidation product for the above-described process), which has a first reaction zone 12 and a second reaction zone 14:

$$\text{product yield (\%)} = \frac{\text{moles of product in first effluent stream} + \text{moles of product in second effluent stream}}{\text{moles of feed supplied}} \times 100$$

With reference again to FIG. 1, in another embodiment of the present invention, at least a portion of the one or more oxidation products are separated from the second effluent stream 34, for example, by using a second separator, such as the second condenser 20 shown in FIG. 1, to produce a second intermediate product stream 36 and a second intermediate feed stream 38. The second intermediate product stream 36 typically contains, but is not limited to, at least a portion of the one or more oxidation products from the second effluent stream 34, as well as other condensables, such as organic acids, aldehydes, ketones, and water. The second intermediate product stream 36 may be fed to additional processing apparatus (not shown) to undergo further separation and purification processes. The second intermediate feed stream 38 contains, but is not limited to, at least a portion of the unreacted oxygen, unreacted $C_3$ to $C_5$ alkane or alkene, or mixture thereof, and possibly reaction by-products such as acetic acid and carbon dioxide, and, possibly, unreacted water and unreacted ammonia, depending upon the starting materials used.

In FIG. 1, the second intermediate feed stream 38 is fed into the optional third reaction zone 18, along with additional oxygen-containing gas 40. More particularly, the additional oxygen-containing gas 40 may be first combined with the second intermediate feed stream 38 and then fed together, as a combined stream (see FIG. 1) to the third reaction zone 18. Alternatively, the additional oxygen-containing gas 40 may be fed to the third reaction zone 18 as a separate feed stream (not shown). In the third reaction zone 18, the unreacted $C_3$ to $C_5$ alkane or alkene, or mixture thereof, and the oxygen (including the unreacted oxygen already present in the second intermediate feed stream 38 and the additional oxygen contributed by the oxygen-containing gas 32) come into contact with the at least one catalyst in the third reaction zone 18 and react with one another to form the desired oxidation products, as well as various side products and by-products, according to the particular types of alkanes and alkenes used.

As is known to those skilled in the art, the condensers will produce a condensed liquid stream and a stream of noncondensible gases. The non-condensibles can be sent to a flare or thermal oxidizer for incineration.

A third effluent stream 42 (see FIG. 1) exits the third reaction zone 18 and typically contains, but is not limited to, one or more oxidation products (e.g., unsaturated carboxylic acid and unsaturated nitrile), unreacted oxygen, and unreacted $C_3$ to $C_5$ alkane or alkene, or mixture thereof, as well as reaction by-products that may include, but are not limited to, acetic acid and carbon dioxide. The third effluent stream may also contain, possibly, unreacted water and unreacted ammonia, depending upon the starting materials used. The third effluent stream 42 may be fed to additional processing apparatus (not shown) to undergo separation and purification processes, to recover the one or more oxidation products.

It is noted that the process of the present invention may be suitably operated as a single-pass reaction or, alternatively, with recycle to one or more of the reaction zones 12, 14, 18, without losing the benefits achieved by the present invention. More particularly, by a single-pass vapor phase catalytic oxidation reaction is meant a vapor phase catalytic oxidation reaction wherein the reactants only pass through each of the reaction zones 12, 14, 18, i.e., over and/or through the catalyst beds, one time. In such an embodiment, there is no recycle of any unreacted reactants nor is there any recycle of reacted materials, regardless of whether they are products or by-products of the reaction. On the other hand, a vapor phase catalytic oxidation reaction with recycle would involve sending a recycle stream comprising at least a portion of at least one of the effluent streams 26, 34, 42, back to one or more of the reaction zones 12, 14, 18.

One alternative embodiment of the process of the present invention utilizes fewer reaction vessels because multiple reaction zones are contained within a single reaction vessel. More particularly, a reactor vessel (not shown) may be adapted to be capable of containing a plurality of reaction zones, such as first and second reaction zones (not shown). Such a reactor vessel may, for example, include an interior baffle or manifold that divides the interior of the reaction vessel into two separate heat exchange zones, i.e., one for each reaction zone 12, 14. Where single reactor vessel is a shell and tube type of reactor, a first half of the tubes therein may extend through one heat exchange zone of the reactor vessel and the second half of the tubes may extend through the other heat exchange zone. Each half of the tubes, respectively, of such a reaction vessel contains a reaction zone. For example, the first half of the tubes might contain the first reaction zone, and the second half of the tubes would contain the second reaction zone. This arrangement of equipment conserves capital by requiring only one reactor vessel, rather than two or more, to contain two or more reaction zones. Optionally, other reactor designs which allow the contact of the feed gas with a suitable catalyst, such as for example plate and frame reactors, can be used instead of shell and tube exchangers. The design and construction of such reactor vessels having multiple reaction zones are well within the skill of persons having ordinary skill in the art.

The process of the invention is an improvement on the STOIC process, and involves monitoring the activity of the catalyst to determine when to change the flow of materials as desired. In one embodiment of the invention, the process is operated in order to maintain a consistently high level of productivity of the overall process. The level of activity can be selected according to various economic and practical, e.g., scheduling and availability, factors. The desired actual activity level can vary depending on plant configuration and other factors. For example, in one embodiment of the invention the flow of materials can be changed when the catalyst has lost at least 25% of its initial activity. In another embodiment, the flow can be changed when the catalyst has lost at least 50% of its initial activity. For the purposes of the invention, the term "initial activity" means the activity at the time the flow of materials is changed or, if no flow change has occurred, means the activity at the start of the steady state reaction.

The catalyst activity can be monitored by measuring performance properties such as conversion, selectivity, yield, etc. according to methods known to those skilled in the art. For example, in one embodiment of the invention, the conversion in a reactor can be monitored and used to decide when to change the flow of materials. In one embodiment of the invention, the conversion of the feed alkane and/or alkene to acrylic acid is used as the measure of activity.

In the process of the invention, the process operates normally until certain conditions are reached, at which time the flow of streams is changed. In the simplest case, involving only one set of catalyst-filled tubes, the gas flow is simply reversed at the desired time. For example, the flow of starting materials to the original reaction zone inlet is halted, and the starting materials are fed to the opposite end of the tubes. This flow reversal can be repeated as desired. This process advantageously can be employed to extend the useful life of the catalyst. Optionally, the reaction zone may be heated in such a way as to remove organic deposits on the catalyst and other sections of the reaction stage (decoke) before reversing the feed stream flow to further improve the performance of the reaction stage.

Examples of variations in operational possibilities include the following. Operating STOIC in a 3-reactor system, where the 3 reactors initially are operated in series with flow directed through the reactors in the order 1-2-3. The order of flow direction later can be altered to 3-2-1, or it can be changed to flow 1-3-2 or 3-1-2, or 2-3-1 or 2-1-3. It is also possible to reverse the flow in only one reactor, or any combination of reactors. In addition, each reactor can be operated in upflow or downflow mode, i.e. the feed can enter either end of a reactor depending on the desired flow combination. Using a notation system where, for reactor X, a downflow feed is designated x and an upflow feed is designated x', the flow of gasses could be, for example, 1-2-3, 1-2'-3,1'-2-3,1'-2'-3',1'-2'-3, or any other possible combination. The optimum process operation is usually determined by factors such as product productivity, flow rates, etc., which may influence operating conditions.

The invention also allows operation with less than the complete number of reactors, and allows one or more reactors to be off-line for catalyst re-pack, regeneration, rejuvenation or hibernation. When not all reactors are on-line, it is possible to operate the remaining reactors at elevated rates (on a single reactor basis) to maintain overall productivity. It is possible to install a $4^{th}$ reactor, for a train that normally uses 3 reactors at once, to allow 1 reactor to always remain idle, while only maintaining 3 condensation/vaporization systems.

In one embodiment of the invention, the system is operated such that the most active catalyst or freshest catalyst is in the first position, i.e. is where the starting material is introduced, where the lowest, or highest, reaction temperature occurs, depending on the hydrocarbon feed composition. This may minimize certain by-product formation. Similarly, the "poorest" catalyst advantageously is in the last position to extend overall catalyst life.

In one embodiment of the invention, the system is operated such that the least active catalyst is in the first position. This is advantageous when it is desired to react hydrocarbons that are more reactive than propane, such as propylene, out of the hydrocarbon feed stream early in the process.

Catalyst-containing tubes of the same or different diameters can be employed in any given reactor. Reactors of different sizes can be employed in a given set of reactors. Both convective heat and mass transfer coefficients are in general directly proportional to the Reynolds number, Re, within a tube. Using tubes of different diameters between reactors, or even having different diameters in zones in a single reactor, may help optimize heat and mass transfer with respect to extent of reaction, reaction heat output, and/or pressure profile. In one embodiment of the invention, the catalyst is contained in tubes and the diameters of all tubes is essentially the same for at least one of the reaction zones. In another embodiment, all of the tubes are not of the same diameter, i.e. at least one tube has a different diameter than another, for at least one of the reaction zones. In one embodiment of the invention, the average diameter of the tubes in one of the reaction zones is different than the average diameter of the tubes in a different reaction zone.

Notwithstanding the broad applicability of the present invention, and without intending to limit the present invention in any way, a first application of the present invention will be described in further detail with respect to a case where propylene and propane are used as the starting material mixture of alkene and alkane and air is used as the oxygen source to produce acrylic acid by vapor phase oxidation, in a single step, in the presence of a suitable mixed metal oxide catalyst. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propylene/propane mixture, whereby high selectivity for acrylic acid can be obtained. This reaction can be conducted usually under atmospheric pressure, but may be conducted under a slightly elevated pressure or slightly reduced pressure. With respect to other mixtures of alkene(s) and alkane(s), the composition of the feed gas may be selected in accordance with the conditions for the mixture of propylene and propane. For example, the feed streams to each reaction zone 12, 14, 18 may be as follows: propane in an amount between 3 vol % and 50 vol %, such as between 7 vol % and 25 vol %, oxygen in an amount between 1 vol % and 50 vol %, such as between 5 vol % and 25 vol %, and water (steam) in an amount between 1 vol % and 50 vol %, such as 5 vol % and 25 vol %, based upon the total volume of the particular feed stream. It is noted that the compositions of the various feed streams of the process need not be the same as one another in order to realize the benefits of the present invention and, in fact, may need to be different from one another, as will be readily understood and determinable by persons of ordinary skill in the art.

Typical reaction conditions for the oxidation of propane or isobutane to acrylic or methacrylic acid may be utilized in the practice of the present invention. General conditions for the process of the present invention are as follows: the reaction temperature can vary from 200° C. to 700° C., but is usually in the range of from 200° C. to 550° C., for example, 300° C. to 450° C., or even 350° C. to 400° C.; the gas space velocity, "SV," in the vapor phase reactor is usually within a range of from 100 to 10,000 hr.$^{-1}$, for example, 300 to 6,000 hr.$^{-1}$, or even 300 to 2,000 hr.$^{-1}$; the average contact time with the catalyst can be from 0.01 to 10 seconds or more, but is usually in the range of from 0.1 to 10 seconds, for example from 2 to 6 seconds; the residence time in each reaction zone can be between 0.5 and 5 seconds, such as between 1 and 3 seconds; the pressure in the reaction zone usually ranges from 0 to 75 psig, such as, for example, no more than 50 psig.

Of course, in the process of the present invention, it is important that the hydrocarbon (i.e., $C_3$ to $C_5$ alkane, or a mixture of $C_3$ to $C_5$ alkanes and alkenes) and oxygen concentrations in the various gas streams be maintained at the appropriate levels to minimize or avoid entering a flammable regime within the reaction zones 12, 14, 18 or especially in the effluent streams 26, 34, 42 of the reaction zones 12, 14, 18. For example, it is preferred that the oxygen concentration in the effluent streams 26, 34, 42 be relatively low to minimize after-burning. In addition, operation of the reaction zones 12, 14, 18 at a low temperature (for example, below 450° C.) is extremely attractive because after-burning becomes less of a problem, which enables the attainment of higher selectivity to the desired oxidation products. The catalysts suitable for use in connection with the process of the present invention, as described hereinabove, typically operate more efficiently at the lower temperature range set forth above, significantly reducing the formation of by-products (such as, but not limited to, acetic acid and carbon oxides), and increasing selectivity to the desired oxidation product (for example, but not limited to, acrylic acid). As a diluting gas, to adjust the space velocity and the oxygen partial pressure, an inert gas such as nitrogen, argon or helium may be employed.

It is noted that where acrylonitrile is the desired oxidation product, the proportion of air to be supplied to the reaction zones 12, 14, 18 is important with respect to the selectivity for acrylonitrile. Namely, high selectivity to acrylonitrile is obtained when air is supplied within a range of at most 25 moles, particularly 1 to 15 moles, per mole of the propane. Moreover, the proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propylene, the composition of the feed gas may be selected in accordance with the aforesaid conditions for propane.

The process of this alternative embodiment of the invention may be conducted at a temperature of, for example, from 200° C. to 480° C., such as from 250° C. to 450° C., or even from 275° C. to 400° C. The gas space velocity, SV, in each of the reaction zones 12, 14, 18 is usually within the range of from 100 to 10,000 $hr^{-1}$, such as from 300 to 6,000 $hr^{-1}$, or even from 300 to 2,000 $hr^{-1}$. The residence time of the reactants in each reaction zone can be between 0.5 and 5 seconds, such as between 1 and 3 seconds. As a diluent gas, for adjusting the space velocity and the oxygen partial pressure, there may be used carbon monoxide, carbon dioxide or mixtures thereof; an inert gas such as nitrogen, argon, helium or mixtures thereof; or mixtures thereof. When ammoxidation of propylene is conducted using the process of the present invention, in addition to acrylonitrile, carbon monoxide, carbon dioxide, acetonitrile, hydrocyanic acid and acrolein may form as by-products. During operation of the process of the present invention to produce unsaturated nitriles, the effluent streams 26, 34, 42 and, therefore, the intermediate feed streams 30, 38 also, are likely to contain unreacted ammonia.

When the process of the present invention is employed to perform oxidation reaction of propane and propylene, in accordance with the present invention, carbon monoxide, carbon dioxide, acetic acid, etc. may be produced as by-products, in addition to acrylic acid. The effluent streams 26, 34, 42 and, therefore, the intermediate feed streams 30, 38 also, are likely to contain water. In addition, an unsaturated aldehyde may sometimes be formed, depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it to a vapor phase catalytic oxidation reaction with a conventional oxidation reaction catalyst for an unsaturated aldehyde.

SPECIFIC EMBODIMENTS OF THE INVENTION

The following examples are given to illustrate the invention and should not be construed as limiting its scope. In the following Examples, "propane conversion" is synonymous with "feed conversion" and is calculated in accordance with the formulas provided hereinabove. Furthermore, "AA yield" means acrylic acid yield and is synonymous with "product yield" and is calculated in accordance with the formulas provided hereinabove.

Unless otherwise specified, all percentages recited in the following Examples are by volume, based on the total volume of the relevant gas stream.

The catalyst is a high-performance Mo/V/Te/Nb mixed metal oxide described in U.S. Pat. No. 7,304,014, assigned to Rohm and Haas Company, and is prepared as follows.

The same mixed metal oxide catalyst is used for all of the Examples described in detail hereinafter. More particularly, a catalyst of nominal composition $Mo_{1.0}V_{0.3}Te_{0.23}Nb_{0.17}Pd_{0.01}O_x$ is prepared in the presence of nitric acid and extracted with oxalic acid in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., is added to a 200 mL rotavap flask. Then, 200 mL of an aqueous solution of ammonium niobium oxalate (0.17M Nb), palladium nitrate hydrate (0.01M Pd), oxalic acid (0.155M) and nitric acid (0.24M) are added thereto. After removing the water via a rotary evaporator with a warm water bath at 50° C. and 28 mm Hg, the solid materials are further dried in a vacuum oven at 25° C. overnight and then are calcined.

Calcination is effected by placing the solid materials in an air atmosphere and then heating them to 275° C. at 10° C./min and holding them under the air atmosphere at 275° C. for one hour; the atmosphere is then changed to argon and the material is heated from 275° C. to 600° C. at 2° C./min and the material is held under the argon atmosphere at 600° C. for two hours. 30 g of the solid materials are ground and added to 100 mL solution of 30% oxalic acid in water. The resulting suspension is stirred at 125° C. for 5 hrs in a Parr reactor, then the solids are collected by gravity filtration and dried in a vacuum oven overnight at 25° C. The catalyst thus obtained is pressed and sieved to 14-20 mesh granules for use in the experimental runs of the reaction system of the following Examples and Comparative Experiments.

For all runs, a two-stage reaction process having a first reaction zone and a second reaction zone in series with the first reaction zone is used to perform vapor phase catalytic oxidation of propane (alkane) to acrylic acid (unsaturated carboxylic acid). Each of the reaction zones is packed with 5 cc of the above-described mixed metal oxide catalyst, which is diluted 1:1 with DENSTONE™ brand spheres, except that no spheres are used in Comparative Experiment 1. The reaction zones are cooled using a molten salt bath.

The reaction system includes an inter-condenser between the first and second reaction zones capable of cooling the effluent stream of the first reaction zone for the purpose of separating at least a portion of the oxidation product (acrylic acid) from the effluent stream prior to being fed to the second reaction zone. The inter-condenser is a typical shell-and-tube heat exchanger familiar to persons having ordinary skill in the art.

For all of the following runs, other than Comparative Experiment 1, reactant starting materials to the first reaction zone comprising 10 vol % propane, 9 vol % water (steam), 17 vol % oxygen, with the remainder being nitrogen, are fed to the two-stage reaction process. A residence time of 1.5 seconds is maintained for the reactants in both reaction zones (stages). The temperatures of both the first and second reaction zone are maintained between 340° C. and 380° C. and they are operated at atmospheric pressure. No recycle is employed. In each run, the compositions of the effluent streams of the first and second reaction zones are analyzed using a gas chromatograph (GC) for gas phase effluent and a liquid chromatograph for liquid phase effluent.

Comparative Experiment 1

Single-Pass, non-STOIC Process (not an Embodiment of the Invention)

In a U-tube reactor, 10.0 cc of catalyst is charged without a diluent and processed with a feed consisting of 7% propane, 14% oxygen, and 23% steam (balance nitrogen). The feed is processed at 3 sec residence time and atmospheric pressure. The reactor is in a salt bath heating medium, and the reactor temperature is adjusted to consistently achieve 85% $O_2$ conversion, corresponding to a nominal 72% propane conversion. The reaction is maintained for about 3700 hrs time-on-stream (TOS) and the rate of catalyst deactivation is determined by continuously plotting catalyst activity vs. time.

Using the catalyst deactivation rate and a U-tube maximum reactor temperature limitation of 400° C., it is determined, via extrapolation, that the catalyst will reach end-of-cycle at ~15,000 hrs TOS and then require replacement.

Comparative Experiment 2

Two-Stage STOIC Operation (not an Embodiment of the Invention)

The procedure of Example 2 of U.S. Pat. No. 7,553,986 is repeated. Separation of the effluent stream of the first reaction zone is achieved using the inter-condenser with chilled water at 4° C. Based on propane conversions determined in this staged process configuration, catalyst deactivation percentage is determined and compared to the results of Comparative Experiment 1. The deactivated catalyst ratios are also determined for each stage of the STOIC process. The results are shown in Table 1.

Comparative Experiment 3

Three-Stage STOIC Operation (not an Embodiment of the Invention)

The procedure of Example 3 of U.S. Pat. No. 7,553,986 is repeated. A 2nd interstage condensed product is obtained and the effluent gas is sent to a 3rd stage reactor. The deactivated catalyst ratio for Stage 3 is determined.

Table 1 below summarizes the deactivated catalyst ratios obtained for each reactor described in Comparative Experiments 1-3.

TABLE 1

|  |  | Lifetime, hrs | Propane processed lbs/lb catalyst | % deactivated |
|---|---|---|---|---|
| Comp. Experiment 1 | Single Pass | 15000 | 1650 | 100% |
| Comp. Experiment 2 | STOIC Stage 1 | 15000 | 1690 | 100% |
|  | STOIC Stage 2 | 15000 | 1100 | 67% |
| Comp. Experiment 3 | STOIC Stage 3 | 15000 | 350 | 21% |

At 15,000 hrs time on stream, the STOIC Stage 1 reactor shows the same level of deactivation as the single pass case. At about 15,000 hrs, both process configurations will need to be shut down for a catalyst change-out.

Example 4

For the Comparative Experiments and Examples, all gas streams are in downflow mode, i.e. each reactor is vertically oriented and the relevant gas feed stream is fed to the top of the relevant reactor. In this Example 4, the 2-stage process of Comp. Experiment 2 is run for 10,000 hrs and then the flow of gasses is altered so that the initial feed stream is fed into the top of the $2^{nd}$ stage reactor, and the gas that exits the inter-condenser of the $2^{nd}$ stage reactor is fed to the top of the $1^{st}$ stage reactor. The process is run for an additional 7500 hrs with this altered flow scheme.

Example 5

In this example, the 3-stage process of Comp. Experiment 3 is run for 10,000 hrs and then the feed flow is altered such that the gas flow goes through Stage 3 first, followed by Stage 2 and then Stage 1, all in downflow mode. The process is run for an additional 10,000 hrs.

Table 2 illustrates the benefits of running with both forward and reverse feed flow per Examples 4 and 5.

TABLE 2

|  | Propane processed, lbs/lb cat. | Time on stream, hrs | Propane processed, lbs/lb cat. | Time on stream, hrs | Total propane processed, lbs/lb cat. | % Deactivated | Total TOS, hrs |
|---|---|---|---|---|---|---|---|
| Normal STOIC |  |  |  |  |  |  |  |
| C.E. 1* | 1690 | 15000 |  |  |  | 100% | 15000 |
| C.E. 2* | 1100 | 15000 |  |  |  | 67% | 15000 |
| C.E. 3* | 350 | 15000 |  |  |  | 21% | 15000 |
| 2-Stage Example 4 |  |  | Reverse flow |  |  |  |  |
| Reactor 1 | 1127 | 10000 | 550 | 7500 | 1680 | 99% | 17500 |
| Reactor 2 | 733 | 10000 | 845 | 7500 | 1580 | 93% | 17500 |
| 3- Stage Example 5 |  |  | Reverse flow |  |  |  |  |
| Reactor 1 | 1127 | 10000 | 233 | 10000 | 1360 | 80% | 20000 |
| Reactor 2 | 733 | 10000 | 733 | 10000 | 1466 | 87% | 20000 |
| Reactor 3 | 233 | 10000 | 1127 | 10000 | 1360 | 80% | 20000 |

*Comparative experiment, not an embodiment of the invention.

In the improved STOIC process disclosed herein for the oxidation of hydrocarbon starting materials to acrylic acid, the flow of reactants is redirected in order to increase run times between catalyst changes. As is clear from Table 2, the reverse flow operation surprisingly increases catalyst lifetime by several thousand hours relative to conventional staged operation. For a 3 or more stage process, it is expected that the extended lifetime can exceed that shown above as the catalysts employed above are not fully deactivated.

What is claimed is:

1. A process for producing unsaturated carboxylic acids or unsaturated nitriles by vapor phase oxidation reaction of their corresponding $C_3$ to $C_5$ alkanes, $C_3$ to $C_5$ alkenes, and mixtures thereof, as a hydrocarbon starting material, using a reaction system having at least two reaction zones arranged in series with one another and at least one catalyst capable of catalyzing the vapor phase oxidation reaction disposed in each of the at least two reaction zones, wherein at least one intermediate effluent stream exits a preceding one of the at least two reaction zones and is at least partially fed to a subsequent one of the at least two reaction zones, said process comprising the steps of:

feeding an initial feed stream comprising the hydrocarbon starting material into a feed point of a first reaction zone of the at least two reaction zones, separating the at least one intermediate effluent stream from the first reaction zone into at least an intermediate product stream comprising an oxidation product selected from the group consisting of an unsaturated carboxylic acid and an unsaturated nitrile, and an intermediate feed stream comprising at least one hydrocarbon starting material selected from the group consisting of an unreacted $C_3$ to $C_5$ alkane, an unreacted $C_3$ to $C_5$ alkene, and mixtures thereof;

feeding an oxygen-containing gas and the intermediate feed stream to a subsequent reaction zone;

the process further comprising:
a. determining the activity of the catalyst in at least one reaction zone;
b. monitoring the activity of the catalyst in each zone to determine the time when the catalyst in any zone has lost at least 25% of its activity;
c. after step b., altering the flow path of at least one of the feed streams such that at least one of the hydrocarbon starting material or the intermediate feed stream is fed to a new feed point, the new feed point being either a feed point of a different reaction zone or a different feed point of the same reaction zone, wherein the catalyst at that new feed point has a higher activity than the activity of the catalyst at the feed point to which the relevant feed was fed prior to this step c.

2. The process of claim 1 wherein steps a., b., and c. are repeated.

3. The process of claim 1 wherein the hydrocarbon starting material comprises at least 50 vol. % propane, based on the volume of the hydrocarbon starting material.

4. The process of claim 1 wherein the hydrocarbon starting material comprises at least 50 vol. % propylene, based on the volume of the hydrocarbon starting material.

5. The process of claim 1 wherein the hydrocarbon starting material comprises at least 5 vol. % propane and from 0.1 to 3.0 vol. % propylene, based on the volume of all gasses fed to the feed point where the hydrocarbon starting material is fed.

6. The process of claim 1 wherein steps a., b., and c. comprise:
a. determining the activity of the catalyst in the reaction zone that receives the initial feed stream;
b. monitoring the activity of the catalyst in the reaction zone that receives the initial feed stream to determine the time when the catalyst in that zone has lost at least 25% of its activity;
c. after step b., altering the flow path of the initial feed stream such that the initial feed stream is fed to a new feed point, the new feed point being either a feed point of a different reaction zone or a different feed point of the same reaction zone, wherein the catalyst at that new feed point has a higher activity than the activity of the catalyst at the feed point to which the relevant feed was fed prior to this step.

7. The process of claim 1 wherein the process produces acrylic acid as the unsaturated carboxylic acid, and wherein there are 2 reaction zones.

8. The process of claim 1 wherein there are 2 reaction zones.

9. The process of claim 1 wherein there are at least 3 reaction zones.

10. The process of claim 1 wherein the alkane is propane, and the alkene is propylene.

11. The process of claim 1 wherein the process is monitored to determine the time when the catalyst in any zone has lost at least 50% of its initial activity.

12. The process of claim 1 wherein the average temperature in the reaction zones is from 200° C. to 480° C.

13. The process of claim 1 wherein the flow of gases through at least one reaction zone can be operated either in feed upflow or feed downflow mode.

* * * * *